(12) United States Patent
Du Clos et al.

(10) Patent No.: US 7,226,995 B2
(45) Date of Patent: Jun. 5, 2007

(54) USE OF C-REACTIVE PROTEIN TO TREAT IMMUNE COMPLEX-MEDIATED RENAL DISEASE

(75) Inventors: Terry Du Clos, Albuquerque, NM (US); Carolyn Mold, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 40 days.

(21) Appl. No.: 10/947,267

(22) Filed: Sep. 23, 2004

(65) Prior Publication Data

US 2005/0281807 A1 Dec. 22, 2005

Related U.S. Application Data

(60) Provisional application No. 60/514,122, filed on Oct. 23, 2003.

(51) Int. Cl.
    C07K 14/435 (2006.01)
(52) U.S. Cl. .................. 530/350; 530/380; 530/324; 530/827
(58) Field of Classification Search ............... 530/350, 530/380, 324, 827
    See application file for complete search history.

(56) References Cited

U.S. PATENT DOCUMENTS

| | | | |
|---|---|---|---|
| 4,857,314 | A | 8/1989 | O'Connor et al. |
| 5,190,917 | A | 3/1993 | Lezdey et al. |
| 5,290,762 | A | 3/1994 | Lezdey et al. |
| 5,593,897 | A * | 1/1997 | Potempa et al. ............. 436/507 |
| 5,783,179 | A * | 7/1998 | Nestor et al. ............... 424/85.2 |
| 6,239,099 | B1 * | 5/2001 | Potempa ........................ 514/2 |
| 6,331,403 | B1 * | 12/2001 | Potempa et al. ............. 435/7.1 |
| 6,342,481 | B1 * | 1/2002 | Leoni et al. .................. 514/18 |
| 6,528,618 | B1 | 3/2003 | Fridkin et al. |
| 6,764,826 | B2 * | 7/2004 | Yeh et al. ..................... 435/7.1 |
| 2002/0119917 | A1 * | 8/2002 | Fridkin et al. ................ 514/12 |
| 2003/0171251 | A1 | 9/2003 | Pepys |

FOREIGN PATENT DOCUMENTS

WO 92/06706 4/1992

OTHER PUBLICATIONS

Bromwich E., British journal of cancer 91 (7) 1236-8, 2004.*
Jabs Wolfram J., Kidney international 68 (5) 2103-10, 2005.*
Szalai, AJ, et al., "Delayed Lupus Onset in (NZB x NZW)F1 mice Expressing a Human C-Reactive Protein Transgene," *Arthritis Rheum.*, 48(6):1602-11 (2003).—paper copy.
Xia, Dongyuan, et al., "Transgenic mice expressing rabbit C-reactive protein are resistant to endotoxemia," *Proc. Natl. Acad. Sci. USA*, 94:2575-2580 (1997).—paper copy.
Mortensen, Richard, et al., "Regulation of phagocytic leukocyte activities by C-reactive protein," *Journal of Leukocyte Biology*, 67:495-500 (2000).—paper copy.
Gershov, Debra, et al., "C-Reactive protein binds to apoptotic cells, protects the cells from assembly of the terminal complement components, and sustains and anti-inflammatory innate immune response: Implications for systemic autoimmunity," *J. Exp. Med.*, 192(9): 1353-1363 (2000).—paper copy.
Hahn, Bevra H., "An overview of the pathogenesis of systemic lupus erythematosus," *Pathogenesis*, pp. 87-96 (2002).—paper copy.
Gescuk, Bryan D. et al., "Novel therapeutic agents for systemic lupus erythematosus," *Curr. Opin. Rheumatol.*, 14:515-521 (2002).— paper copy.
Karpouzas, George et al., "Systemic lupus erythematosus," *Targeted Therapies in Rheumatology*, J.S. Smolen and P.E. Lipsky editors, London, 563-581 (2003).—paper copy.
Volanakis, John E.,"Human C-reactive protein: expression, structure, and function," *Molecular Immunology*, 38:189-197 (2001).— paper copy.
Heuertz, Rita M., "Inhibition of C5a des Arg-induced neutrophil alveolitis in transgenic mice expressing C-reactive protein," *Am. J. Phys.*, 266:L649-L654 (1994).—paper copy.
Du Clos, Terry et al., "Decreased autoantibody levels and enhanced survival of (NZB x NZW)F1 mice treated with C-Reactive Protein," *Clinical Immunology and Immunopathology*, 70(1):22-27, (1994).— paper copy.
Du Clos, Terry et al., "Monoclonal antibody for DNA measurement in biological fluids," *J. of Immunological Methods*, 88:185-192 (1986).—paper copy.
Theofilopoulos, Argyrios N. et al., "Murine Models of systemic lupus erythematosus," *Advances in Immunology*, 37:269-391 (1985).—paper copy.
Spronk, P.E., "Patients with systemic lupus erythematosus and Jaccoud's arthropathy: a clinical subset with an increased C reactive protein response?," *Annals of Rheumatic Diseases*, 51:358-361 (1992).—paper copy.
Pepys, M. B. et al., "C-Reactive protein in SLE," *Clinics in Rheumatic Diseases*, 8(1):91-103 (1982).—paper copy.
Baltz, Marilyn L. et al., "In vivo turnover studies of C-reactive protein,", *Clin. Exp. Immunol.*, 59:243-250 (1985).—paper copy.
Tipping, P. G. et al., "Immune Modulation with interleukin-4 and interleukin-10 prevents crescent formation and glomerular injury in experimental glomerulonephritis," *Eur. J. Immunology*, 27:530-537 (1997).—paper copy.
Kitching, Richard A. et al., "Interleukin-4 and interleukin-10 attenuate established crescentic glomerulonephritis in mice," *Kidney International*, 52:52-59 (1997).—paper copy.
Clynes R. et al., "Uncoupling of immune complex formation and kidney damage in autoimmune glomerulonephritis," *Science*; 279: 1052-4 (1998).—on CD-ROM.

(Continued)

Primary Examiner—David Lukton
(74) Attorney, Agent, or Firm—Henry D. Coleman; R. Neil Sudol; William J. Sapone

(57) ABSTRACT

The present invention relates to a method of treating or preventing kidney disease in an animal subject including administering an effective amount of C-reactive protein to the animal subject. The kidney disease may be associated with systemic lupus erythematosus.

10 Claims, 6 Drawing Sheets

OTHER PUBLICATIONS

Du Clos, Terry, "C-reactive protein reacts with the U1 small nuclear ribonucleoprotein," *J. Immunol.*, 143(8):2553-9 (1989).—on CD-ROM.

Marnell L.L. et al., "C-reactive protein binds to Fc gamma RI in transfected COS cells," *J. Immunol.*, 155:2185-93 (1995).—CD-ROM.

Bharadwaj D. et al., "The major receptor for Creative protein on leukocytes is Fcgamma receptor II," *J Exp Med.*, 190:585-90 (1999).—on CD-ROM.

Mold C. et al. "C-reactive protein mediates protection from lipopolysaccharide through interactions with Fc gamma R," *J Immunol.*, 169:7019-25 (2002).—CD-ROM.

Wakayama H., et al., "Abolition of anti-glomerular basement membrane antibody-mediated glomerulonephritis in FcR -deficient mice," *Eur J Immunol.*, 30:1182-90 (2002).—on CD-ROM.

Moore KW. et al., "Interleukin-10 and the Interleukin-10 receptor," *Ann Rev Immunol*, 19:683-765 (2001).—on CD-ROM.

Du Clos TW, "Function of C-reactive protein," *Ann Med*, 32:274-8 (2000).—on CD-ROM.

Robey FA., et al., "Binding of C-reactive protein to chromatin and nucleosome core particles. A possible physiological role of C-reactive protein," *J Biol Chem*, 259(11):7311-6 (1984).—on CD-ROM.

Stein MP. et al., "C-reactive protein binding to murine leukocytes requires Fc gamma receptors," *J. Immunol*, 164:1514-20 (2000).—on CD-ROM.

Walport MJ, "Lupus, DNase and defective disposal of cellular debris," *Nat Genet*, 25: 135-6 (2000).—on CD-ROM.

Carroll MC., "A protective role for innate immunity in autoimmune disease," *Clin Immunol*, 95(1):S30-8 (2000).—on CD-ROM.

Du Clos TW, "C-reactive protein as a regulator of autoimmunity and inflammation," *Arthritis Rheum*, 48:1475-7 (2003).—on CD-ROM.

Xia D, Samols D, "Transgenic mice expressing rabbit C-reactive protein are resistance to endotoxemia," *Proc Natl Acad Sci USA*, 94:2575-80 (1997).—on CD-ROM.

Jonuleit H, Schmitt E, "The regulatory T cell family:Distinct subsets and threir interrelations," *J. Immun.*, 171:6323-7 (2003).—on CD-ROM.

Tarzi, RM et al., "Both Fc gamma receptor I and III mediate disease in accelerated nephrotoxic nephritis," *Am. J. Pathol.*, 162:1677-83

Burlingame RW., et al. "The effect of the acute phase proteins on clearance of chromatin from the circulation of normal mice," *J Immunol.* 156:4783-8 (1996).—on CD-ROM.

Mold C., et al., "Serum amyloid P component and C-reactive protein opsonize apoptotic cells for phagocytosis through Fcgamma receptors," *J. Autoimmun*, 19:15 147-54 (2002).—on CD-ROM.

Bickerstaff MC., et al., "Serum amyloid P component controls chromatin degradation and prevents antinuclear autoimmunity," *Nat Med*, 5:694-7 (1999).—on CD-ROM.

Yin, Z., et al., "IL-10 regulates murine lupus," *J. Immuol.*, 169:2148-55 (2002).—on CD-ROM.

Samuelsson, A. et al., "Anti-inflammatory activity of IVIG mediated through the inhibitory Fc receptor," *Science*, 291:484-6 (2001).— on CD-ROM.

Kitching AR., et al., "Endogenous interleukin-10 regulates Th 1 responses that induce cresccentic glomerulonephritis," *Kidney Int*, 57:518-25 (200).—on CD-ROM.

Groux Het al. A CDA+ Tcell subset inhibits antigen-specific T-cell responses and prevents colitis. Nature 1997;389:737-42.—on CD-ROM.

Russell, A. I. et al., "Polymorphism at the C-reactive protein locus influences gene expression and predisposes to systemic lupus erythematosus," *Human Molecular Genetics*, 13(1):137-147 (2004).—CD-ROM.

Du Clos, "*C-Reactive Protein as a Regulator of Autoimmunity and Inflammation*," Editorial, Arthritis & Rheumatism, vol. 48, No. 6, Jun. 2003, pp. 1475-1477.

Du Clos, "*Function of C-Reactive Protein*," Trends in Molecular Medicine, The Finnish Medical Society Duodecim, Ann Med 2000; 32:274-278.

Du Clos et al., "*The Role of C-Reactive Protein in the Resolution of Bacterial Infection*," Pathogenesis and Immune Response, IF 140307, 2001 Lippincott Williams & Wilkins 0951-7375, pp. 1-5.

Mold et al., "C-Reactive Protein Mediates Protection from Lipopolysaccharide Through Infections With FcγR[1]," The Journal of Immunology, 2002 The American Association of Immunologists, Inc., 2002, 169, pp. 7019-7025.

Du Clos et al., "*An Activator of Innate Immunity and a Modulator of Adaptive Immunity*," Immunologic Research 2004; 30/3: 261-277.

Szalai et al., "*Delayed Lupus Onset in (NZB x NZW)$F_1$ Mice Expressing a Human C-Reactive Protein Transgene*," Arthritis & Rheumatism, vol. 48, No. 6, Jun. 2003, pp. 1602-1611, 2003.

Benoist et al., "*Mast Cells In Autoimmune Disease*," Insight Progress, Nature, vol. 420, Dec. 19-26, 2002, Nature Publishing Group, pp. 875-878.

Pelsue et al., "*Lymphadenopathy, elevated serum IgE levels, autoimmunity, and mast cell accumulation in flaky skin mutant mice*,"Eur. J. Immunol., 1998, 28: 1379-1388.

\* cited by examiner

USE OF C-REACTIVE PROTEIN TO TREAT IMMUNE COMPLEX-MEDIATED RENAL DISEASE

RELATED APPLICATIONS

This application claims the benefit of priority of U.S. Provisional Application No. 60/514,122, filed Oct. 23, 2003.

REFERENCE TO GOVERNMENT GRANT

This invention was made with government support under a VA merit review and grant R01-AI28358 awarded by the National Institutes of Health. The U.S. government may have certain rights in this invention.

FIELD OF THE INVENTION

The invention relates generally to treatment of renal disease. More specifically, the present invention relates to treatment of immune complex-mediated renal disease using C-reactive protein (CRP).

BACKGROUND OF THE INVENTION

Systemic lupus erythematosus (SLE) is a systemic immune complex disease of humans that affects multiple organ systems. The disease is characterized by rashes, arthritis, lung disease, and kidney disease. It occurs mostly in women and usually strikes during young adulthood. Perhaps the most severely affected organ is the kidney, and glomerulonephritis is the major cause of morbidity and mortality in patients with SLE. The current standard treatment for lupus nephritis is the alkylating agent cyclophosphamide, a strong immunosuppressive drug. Although treatment is generally effective, the drug has many side effects including infections, sterility, hair loss, and malignancy.

A wide variety of agents have been used to treat SLE. These agents may act either by interfering with collaborations between B and T lymphocytes, directly eliminating effector cells, or by blocking individual cytokines. Biological agents have had various levels of success in treating animal models of SLE. However, most agents require repeated treatment with high concentrations of mAb or protein antagonists.

The most commonly studied animal model of human SLE is the NZB X NZW F1 female mouse (NZB/W). This mouse shares many features with the human disease including severe proliferative glomerulonephritis, which is the major cause of death in the mice. The mice have high levels of circulating immune complexes (IC), which interact with Fc gamma receptors (FcR) in the kidney to induce nephritis. A second mouse model of human SLE is the MRL-Fas$^{lpr}$ mouse, which exhibits a more rapid progression of disease than the NZB/W mouse.

The innate immune system plays an important role in autoimmunity. One way in which the innate immune system molecules may affect autoimmunity is through the recognition and clearance of autoantigens released from apoptotic or necrotic cells. Other possible mechanisms for protecting against autoimmune-mediated inflammation include altering the cytokine response to inflammatory stimuli and by redirecting the adaptive immune system.

C-reactive protein (CRP) is the prototypic acute phase reactant in man and a component of the innate immune system. CRP binds to nuclear antigens that are the target of the autoantibodies of patients with SLE as well as to damaged membranes and microbial antigens. CRP activates the classical complement pathway and interacts with phagocytic cells through FcR. CRP is protective against various inflammatory states including endotoxin shock and inflammatory alveolitis. CRP protection against endotoxin shock requires FcR and is associated with FcR-dependent induction of interlukin-10 (IL-10) synthesis by macrophages.

It has been reported that CRP was protective against the accelerated disease in NZB/W mice injected with chromatin. It has also been demonstrated that NZB/W mice transgenic for human CRP had a delayed onset of proteinuria and enhanced survival. The ability of CRP to prolong survival in NZB/W mice has been attributed to increased binding and clearance of autoantigens or immune complexes. However, the ability of CRP to regulate acute inflammation suggests an alternative mechanism for its beneficial effects in SLE.

What is needed is an effective treatment for kidney disease (including that caused by SLE) that does not have the serious side effects attendant with cyclophosphamide treatment. What is also needed is an effective way to modify the response to autoantigens and thereby delay or even reverse nephritis caused by, for example, SLE.

SUMMARY OF THE INVENTION

In accordance with the invention, there is provided a method of treating or preventing kidney disease in an animal subject, the method comprising administering an effective amount of C-reactive protein to the animal subject.

According to various embodiments, there is provided a method of treating or preventing kidney disease associated with systemic lupus erythematosus in a patient, comprising administering an effective amount of a C-reactive protein to the patient.

According to various embodiments, there is provided a method of treating or preventing kidney disease in a patient comprising, administering an effective amount of a therapeutic material chosen from a C-reactive protein, a metabolite of C-reactive protein, and a combination thereof.

According to various embodiments, there is provided a pharmaceutical composition comprising a therapeutic material chosen from C-reactive protein, a metabolite of a C-reactive protein, and a combination thereof and a pharmaceutically acceptable excipient or carrier.

According to various embodiments, there is provided a method for producing a pharmaceutical composition comprising admixing a therapeutic material chosen from C-reactive protein, a metabolite of C-reactive protein, and a combination thereof and a pharmaceutically acceptable excipient or carrier.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate at least one embodiment of the invention and together with the description, serve to explain the principles of the invention.

FIG. 3A is a kidney from untreated control mice C57BL/6. FIG. 3B is a kidney from C57BL/6 mouse with NTN (day 11 after anti-GBM) showing increased glomerular cellularity with hypertrophy of glomerular cells, neutrophilic glomerular infiltrates (small arrows), intraglomerular fibrin thrombi (large arrow), fluid leakage into Bowman's space, and early crescent formation. Adjacent tubules contain protein rich fluid (arrowhead). FIGS. 3C and 3D are kidneys from CRP-treated C57BL/6 mice with NTN. For example, FIG. 3C, a picture of kidneys from late CRP treatment mice, or FIG. 3D, a picture of kidneys from early CRP treatment, shows that treatment markedly attenuates the glomerular pathology associated with NTN (day 11).

DESCRIPTION OF THE EMBODIMENTS

Figure 1A:
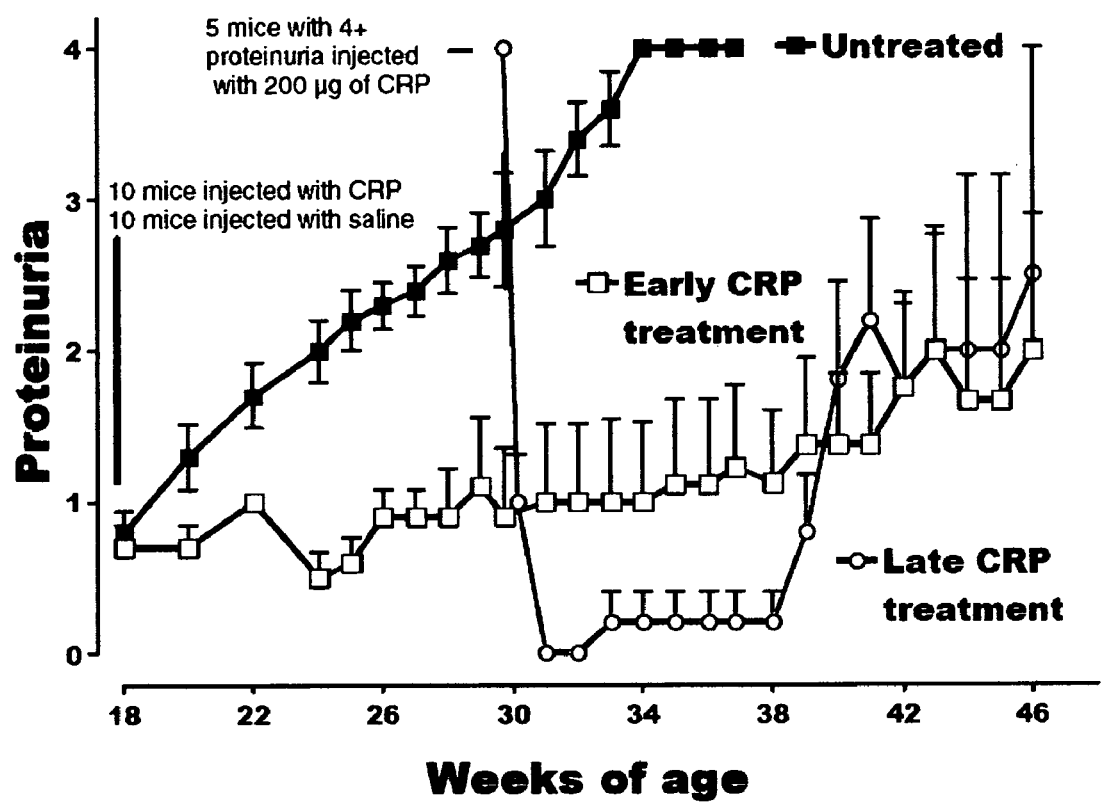
FIG. 1A is a graph illustrating the effect of CRP treatment of NZB/W mice on the development of proteinuria and the reversal of proteinuria.

Reference will now be made in detail to the present embodiment(s) (exemplary embodiments) of the invention, at least one example of which is illustrated in the accompanying drawings.

CRP is an acute phase serum protein that provides innate immune recognition, opsonization, and regulation of autoimmunity and inflammation. CRP may bind several autoantigens in SLE, for example SmD1, and 70K proteins of Sm and RNP, histones, and chromatin. CRP may activate complement and may bind to FcRI and FcRII in man and mouse. CRP is a natural product found in the serum of people, and it is believed to be nontoxic.

Human CRP may be purified from human pleural effusion fluid. T. W. Du Clos, "C-reactive protein reacts with the U1 small nuclear ribonucleoprotein," *J. Immunol.*, 143:2553-2559 (1989). For example, human pleural fluids may be obtained from discarded drains of patients undergoing surgery. The fluids may be clarified by high speed centrifugation. The CRP may be partially purified by affinity chromatography and then may be further purified by gel filtration chromatography. The CRP may then be further purified by affinity chromatography on PC-Sepharose. For final purification, the protein may be purified by mono Q based FPLC. A major band should be seen at about 25 kDa. The final preparation may then be filter-sterilized and an endotoxin contamination may be measured by a limulus-based assay from Cambrex (East Rutherford, N.J.). Endotoxin may be removed using Acticlean Etox (Sterogene Bioseparations Inc., Carlsbad, Calif.) to reduce preparations to less than 0.3 ng of endotoxin/mg of protein.

According to various embodiments, the CRP may be used for treatment or prevention purposes in the form of a pharmaceutical composition. This pharmaceutical composition may comprise 100% pure CRP. Moreover, the CRP may not be 100% pure. For example, the CRP may be less than 100% pure. Metabolites of CRP may also be used. For example, the pharmaceutical composition may comprise a mixture of 100% pure CRP and less than 100% pure CRP, such as a metabolite of CRP. The CRP may be in a form chosen from a solid, semi-solid, and liquid.

The pharmaceutical composition may also comprise a pharmaceutically acceptable excipient or carrier. The pharmaceutically acceptable excipient or carrier may be in a form chosen from a solid, semi-solid, and liquid. The pharmaceutically acceptable excipient or carrier may be chosen from a starch, crystalline cellulose, sodium starch glycolate, polyvinylpyrolidone, polyvinylpolypyrolidone, magnesium stearate, sodium laurylsulfate, sucrose, gelatine, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the CRP with a pharmaceutically acceptable excipient or carrier.

The pharmaceutical composition may be in a form chosen from sterile isotonic aqueous solutions, pills, drops, paster, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intestinal, parenteral, oral, buccal, nasal, intramuscular, transcutaneous, transdermal, intranasal, intraperitoneal, and topical.

The animal subject animal may be chosen from, for example, a human, a mouse, a mammal, and other animals. The animal subject may have renal disease, such as kidney disease.

The CRP may be administered in an effective amount to treat or prevent kidney disease. One of ordinary skill in the art would be readily able to determine this amount by taking into consideration several variables including, but not limited to, the animal subject, age, sex, weight, previous medical history, other medications, etc. For example, the dose of CRP for mice may range from at least about 50 μg to at least about 200 μg.

The dose of CRP may be administered prior to the onset of a medical condition, such as SLE, or after the onset of a medical condition, such as high grade proteinuria. For example, the dose of CRP may be administered for the purpose of treating active kidney disease and/or preventing kidney disease. The kidney disease may be associated with SLE.

EXAMPLE 1

NZB/W Mice

The onset of proteinuria in NZB/W mice occurs at about 20 weeks of age. They undergo a gradual, progressive increase of proteinuria that leads to renal failure, severe glomerulonephritis, and 50% mortality by about 36 weeks of age. In the NZB/W mouse model of SLE, mice develop anti-dsDNA antibodies and die of immune complex glomerulonephritis at about 36 weeks of age.

As shown in FIG. 1A, 18 week old NZB/W female mice obtained from Jackson Laboratories (Bar Harbor, Me.) were divided into two groups (n=10). One group was injected with saline (untreated control) and the other group was injected subcutaneously with 200 μg of CRP (early CRP treatment).

Disease activity was monitored two ways. Proteinuria was measured weekly by using Chemstrips (Roche, Nutley, N.J.). Grades of proteinuria were expressed as "0" level on the proteinuria axis indicates a negative result, a "1+" level indicates a trace amount, a "2+" level indicates 30 mg/dl, a "3+" level indicates a 100 mg/dl, and a "4+" level indicates 500 or more mg/dl.

Moreover, autoantibody levels, such as anti-dsDNA antibody levels, were measured by bleeding the mice monthly and collecting the serum. IgG antibody to double stranded DNA (dsDNA) was measured using a 1/400 dilution of serum. Rubin, R. L., "Enzyme-linked immunosorbent assay for anti-DNA and antihistone antibodies," *Manual of Clinical Laboratory Immunology*, N. R. Rose et al. editors, ASM, Washington, 744-749 (1986). An anti-dsDNA mAb was used as a plate standard.

When the untreated control NZB/W mice had developed significant proteinuria at 30 weeks of age, 5 mice from this group with 4+ proteinuria were subcutaneously injected with 200 μg CRP (late CRP treatment). Proteinuria was measured daily for the first week and weekly thereafter.

Mice were euthanized for humanitarian reasons if they developed 4+ proteinuria accompanied by weight loss of greater than 20%. Euthanized mice were included as deaths in the survival curves.

As shown in FIG. 1A, the mice that were injected with CRP at 18 weeks of age had a marked delay (16 weeks) in the onset of high grade proteinuria (>3+) as compared to the saline-injected mice. The mice that received saline and no rescue dose of CRP at 30 weeks of age all developed high grade proteinuria (>4+) at 34 weeks of age despite the fact that the five mice with the highest grade proteinuria were removed at 30 weeks of age for CRP treatment. In the group of mice rescued by CRP at 30 weeks of age, there was a rapid decrease in proteinuria within 2 days of treatment. The mice became completely free of measurable proteinuria and significant proteinuria did not return until 12 weeks after CRP treatment.

Figure 1B:
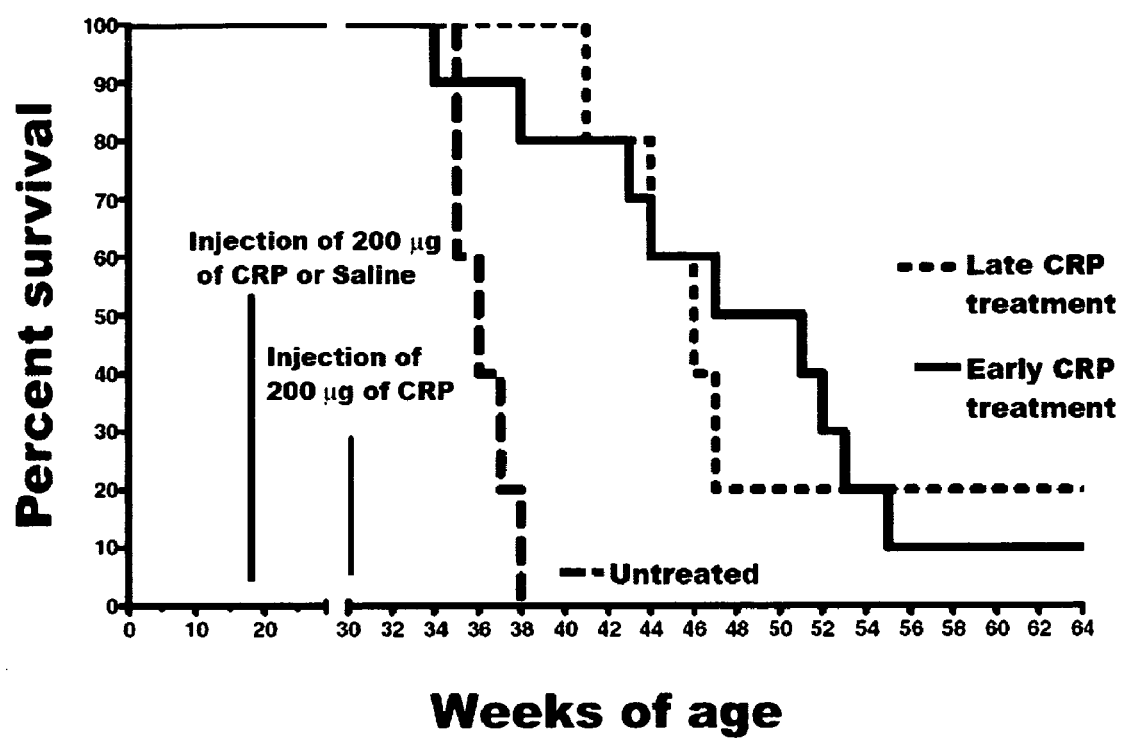
FIG. 1B is a graph illustrating the survival rates of NZB/W mice treated with CRP before or after the onset of lupus nephritis.

As shown in FIG. 1B, proteinuria scores were consistent with survival levels. The median survival was increased from 41 weeks in controls to 52 weeks in CRP-treated mice. The untreated control mice died between 35 and 38 weeks of age and the median survival time was 36 weeks. The early CRP treated mice lived much longer with a median survival age of 49 weeks. These mice developed proteinuria more slowly than the untreated control mice. The untreated control mice developed 3+ proteinuria at a median age of 26.5 weeks as compared to 42.5 weeks for the CRP-treated mice. Interestingly, the late CRP treated mice again developed proteinuria at a similar age as the early CRP treated mice and had a similar median survival age of 46 weeks.

The primary mechanism for the development of renal pathology in NZB/W mice is the deposition of IC in the kidneys. These IC are made up in part of dsDNA and autoantibodies to dsDNA. Development of anti-dsDNA Ab correlates in time with the development of nephritis in untreated NZB/W mice. NZB/W mice treated with CRP either early or late did not have significantly reduced IgG anti-dsDNA antibodies.

EXAMPLE 2

NTN in C57BL/6 Mice

Although NZB/W mice are considered the classical IC mediated nephritis model, other animal models of IC-mediated nephritis have been developed. NTN is a well-described model of nephritis, which has been extensively used as a surrogate model for SLE nephritis. The disease is induced by injecting animals with rabbit IgG in CFA initially and then about one week later with rabbit anti-GBM Ab. Mice rapidly develop high grade proteinuria.

To prepare anti-mouse GBM antibody, rabbits were immunized with purified mouse glomeruli. The purification of mouse glomerular basement membrane and immunization of rabbits is known in the art, for example, Wakayama, H., "Abolition of anti-glomerular basement membrane antibody-mediated glomerulonephritis in FcR gamma-chain deficient mice," *Eur. J. Immunol.*, 30:1182-1190.

The specificity of the effect of CRP for SLE-related nephritis was tested via the effect of CRP on accelerated NTN. At 6-8 weeks of age, C57BL/6 mice (National Cancer Institute, Frederick, Md.) were intraperitoneally injected (day -7) with 0.25 mg of rabbit IgG in complete Freund's adjuvant (CFA, Sigma, St. Louis, Mo.). NTN was induced one week later by intravenously injecting the mice with three daily injections (day 0, 1 and 2) of 100 μl rabbit anti-glomerular basement membrane (anti-GBM) serum.

A single subcutaneous injection of saline (untreated control) or 200 μg of human CRP (early CRP treatment) was given for treatment either at the same time as the first anti-GBM injection, or 9-10 days later, after the mice had developed 5+ proteinuria (late CRP treatment).

Disease activity was monitored daily by measuring proteinuria using Albustix (Bayer, West Haven, Conn.). Grades of proteinuria were expressed as "0" level on the proteinuria axis indicates a negative result, a "1+" level indicates a trace amount, a "2+" level indicates 30 mg/dl, a "3+" level indicates a 100 mg/dl, a "4+" level indicates 300 mg/dl, and a "5+" indicates >2000 mg/dl.

The results show that CRP injection results in a rapid decrease in proteinuria in NTN. For example, injection of CRP either before or after induction of NTN suppressed proteinuria and glomerular pathology. The untreated control mice underwent a rapid increase of proteinuria that remained stable for at least 16 days after induction. In the early CRP treated mice, there was a complete absence of significant proteinuria (0 or 1+) in 4/6 mice for the duration of the examination period. The other two CRP-treated mice developed 5+ proteinuria on days 8 and 10. The late CRP treated mice showed a rapid and complete reversal of proteinuria and remained free of significant proteinuria for the duration of the experiment.

Figure 2:
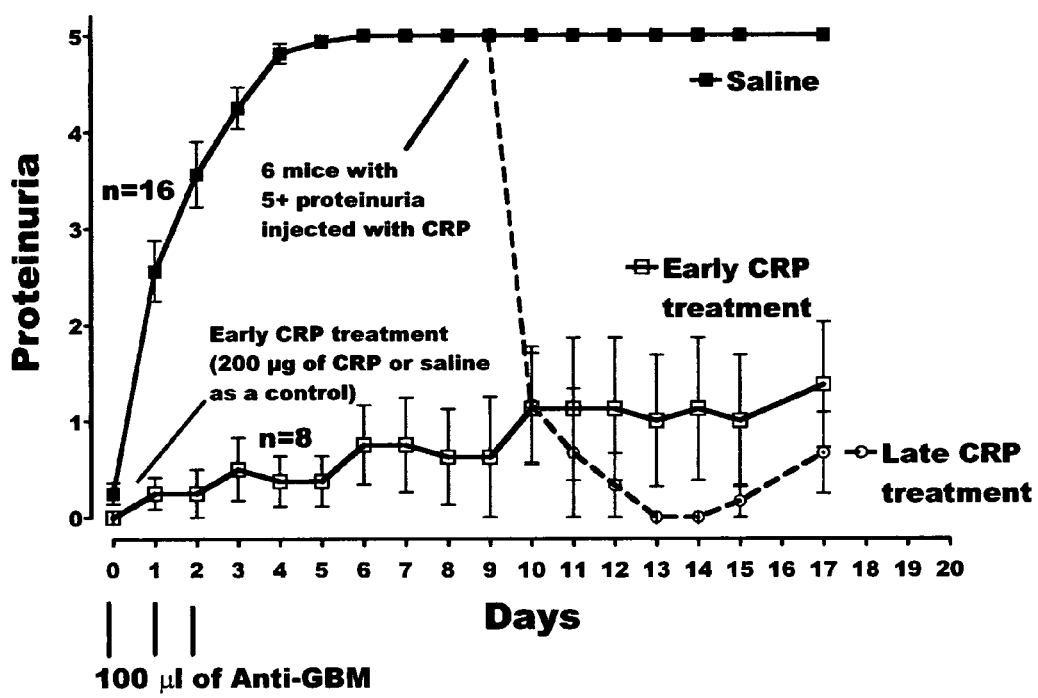
FIG. 2 is a graph illustrating the effect of a single injection of CRP treatment of C57BL/6 mice with nephrotoxic nephritis (NTN) on the development of proteinuria and the reversal of proteinuria. Mice were immunized with rabbit IgG on day -7 and injected with rabbit antibody to mouse glomeruli on days 0, 1 and 2 to induce NTN. CRP treatment was a single injection of 200 μg on day 0 or day 9.
Figure 3:
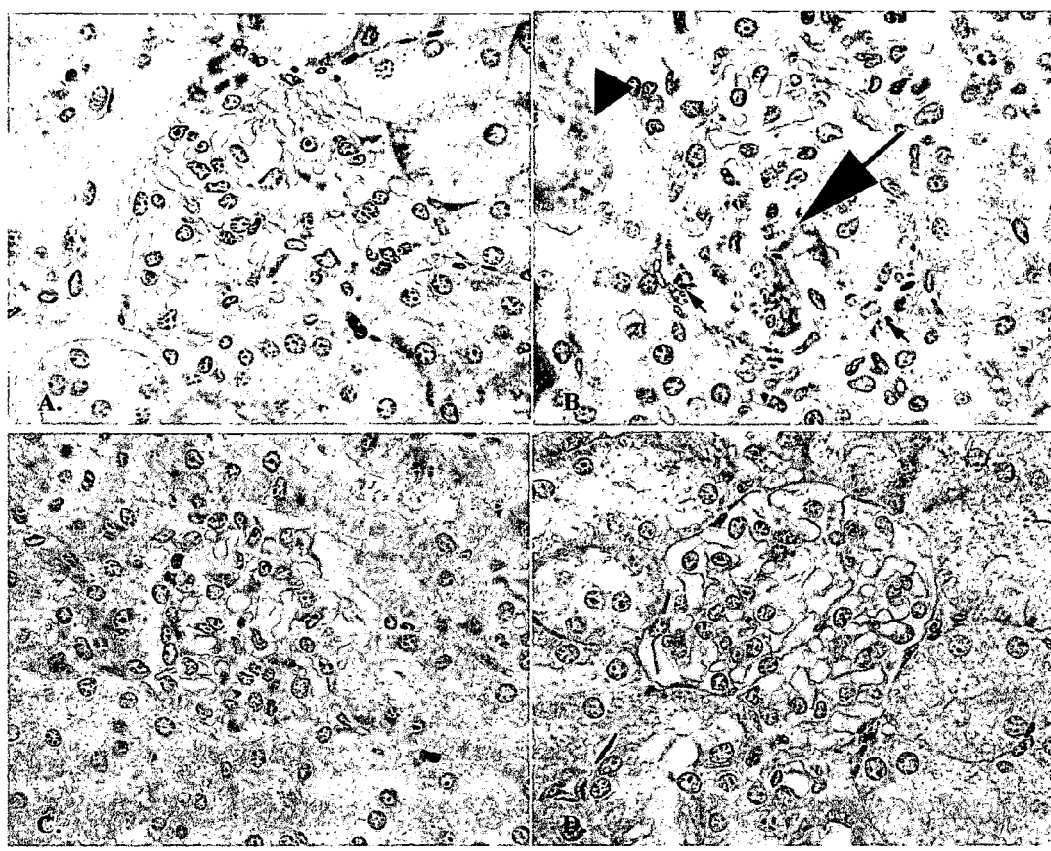
FIGS. 3A-D are a series of pictures illustrating that CRP decreases renal pathology in NTN mice.

The mice from the experiment shown in FIG. 2 were sacrificed on day 11, and their kidneys fixed and examined microscopically (FIG. 3). The kidneys were removed and fixed for two hours in Bouin's solution and then transferred to 70% ethanol. They were then embedded in paraffin and 2 micron sections cut and stained with hematoxylin and eosin (H&E) or with periodic acid-Schiff (PAS) reagent. The sections were examined in a blinded manner and scored for glomerular and other renal changes. Glomerular lesion scores were assigned on a 4 point scale based on the number of glomeruli involved and the severity of the lesions (1, <10%, minimal; 2, 10-25%, mild; 3, 50%, moderate; 4, >50%, marked). Overall lesion scores were also determined and included tubular degeneration and proteinuria and interstitial and perivascular inflammation. Thirty glomeruli in each kidney were examined.

Significant changes in the NTN control mice were observed, primarily in the glomeruli capillaries with karyorrhectic debris, glomerular hypercellularity, hypertrophy of glomerular mononuclear cells, protein rich fluid exudation into the glomerulus and bridge formation between podocytes and parietal epithelium (early crescent formation). PAS staining (not shown) revealed a slight increase in PAS positive material in glomerular tufts and a prominent disruption of the organization of the basement membranes in NTN control mice.

In contrast, glomeruli from both groups of CRP-treated mice appeared normal on PAS staining. The scored pathological changes observed in glomeruli on H&E staining were compared for the three NTN groups and untreated C57BL/6 mice. Both groups of CRP-treated mice had significantly decrease glomerular lesion scores compared to NTN control mice. Overall lesion scores including tubular changes, perivascular and interstitial inflammation as well as glomerular changes were also higher in the NTN control mice compared to both CRP treatment groups. In contrast to the decreased pathology in glomeruli from CRP-treated mice, examination of frozen sections by immunofluorescence showed similar levels of both rabbit and mouse IgG in glomeruli of CRP and NTN control mice. These results are consistent with suppression of the inflammatory response in the kidney by CRP.

EXAMPLE 3

IL-10

IL-10 is a potent anti-inflammatory cytokine, which has profound effects on the inflammatory response and is important for the generation of regulatory T cells. It has been demonstrated that IL-10 may modulate the severity of IC-mediated diseases including lupus nephritis and NTN.

Figure 4:
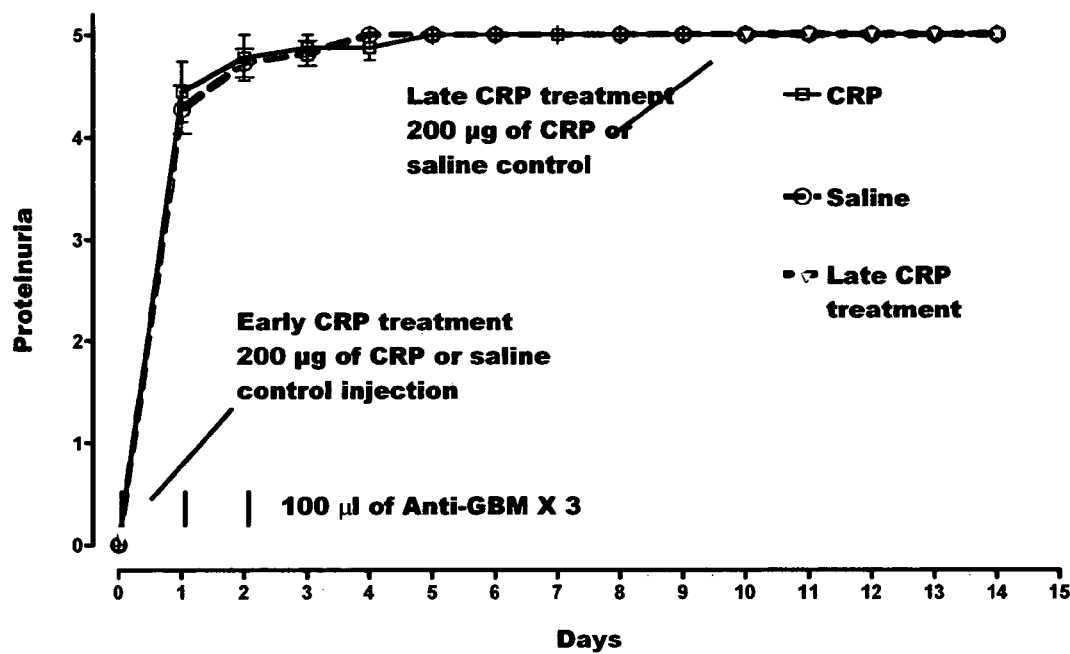
FIG. 4 is a graph illustrating the effect of a single injection of CRP treatment of C57BL/6 IL-10 deficient mice with NTN on the development of proteinuria and reversal of ongoing proteinuria.

At 6-8 weeks of age, C57BL/6 IL-10-deficient mice (obtained from Jackson Laboratories, Bar Harbor, Me., and bred at the Albuquerque Veterans Administration Animal Facility) were injected (day -7) intraperitoneally with 0.25 mg of rabbit IgG in complete Freund's adjuvant (CFA, Sigma, St. Louis, Mo.). NTN was induced one week later (day 0, 1 and 2) by intravenously injecting the mice with three daily injections (day 0, 1 and 2) of 100 µl rabbit anti-GBM serum (FIG. 4). A single subcutaneous injection of 200 µg of human CRP was given for treatment either at the same time as the first anti-GBM injection, or 9 days later, after the mice had developed 5+ proteinuria. Control mice were treated with an equal volume of saline.

Disease activity was monitored daily by measuring proteinuria using Albustix (Bayer, West Haven, Conn.). Grades of proteinuria were expressed as "0" level on the proteinuria axis indicating a negative result, a "1+" level indicating only a trace amount, a "2+" level indicating 30 mg/dl, a "3+" level indicating a 100 mg/dl, a "4+" level indicating 300 mg/dl, and a "5+" indicating >2000 mg/dl.

The IL-10 deficient mice experienced a rapid onset of severe proteinuria that persisted throughout the experiment. CRP was completely ineffective in treating NTN in IL-10 deficient mice either when injected at the time of anti-GM Ab or at day 9 after. It is believed, without being limited to any particular theory, that CRP must rapidly initiate an IL-10 dependent anti-inflammatory process. It appears that a function of CRP during the acute phase response is to limit tissue damage and modulate acute inflammation.

EXAMPLE 4

MRL/lpr Mice

Figure 5:
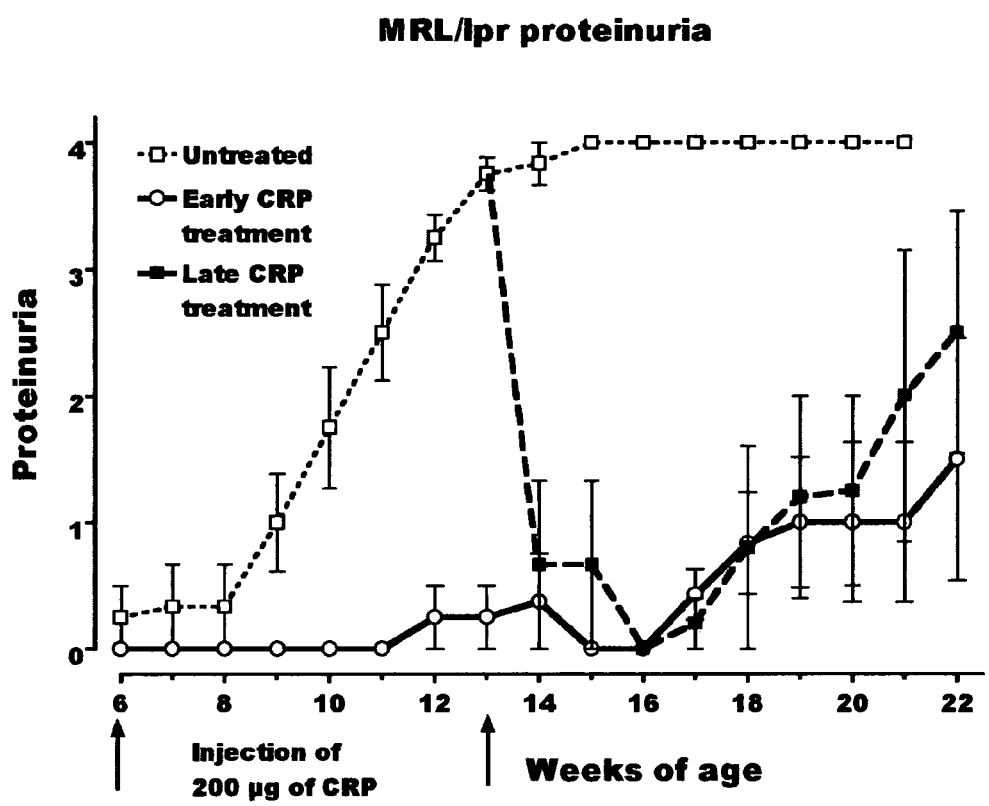
FIG. 5 is a graph illustrating the effect of CRP treatment of MRL/lpr mice on the development of proteinuria and reversal of ongoing proteinuria.

MPL/lpr mice are often used as an animal model of human SLE because it develops the disease earlier in life, such as at 8 weeks of age. The same procedure was used as in Example 1 except that MRL/lpr mice were used. As shown in FIG. 5, CRP treatment was started at 6 weeks of age and completely prevented the onset of significant proteinuria for at least 14 weeks. CRP treatment has also prevented the development of lymphadenopathy and delayed the development of anti-dsDNA antibodies. It appears that the effectiveness of CRP treatment may extend to multiple models of autoimmunity.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10," includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a dose of CRP" includes two or more different doses of CRP. As used herein, the term "include" and its grammatical variants are intended to be non-limiting, such that recitation of items in a list is not to the exclusion of other like items that can be substituted or added to the listed items.

The disclosures of all of the references, including journal articles and patents, cited herein are expressly incorporated by reference in their entirety.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A method of treating kidney disease associated with glomerulonephritis in an animal subject in need of treatment comprising administering an effective amount of a therapeutic material chosen from a C-reactive protein, a metabolite of C-reactive protein, and a combination thereof to the animal subject for a time and under conditions effective to mitigate kidney disease associated with glomerulonephritis.

2. The method of claim 1, wherein the animal subject is a mammal.

3. The method of claim 1, wherein the animal subject is a human.

4. The method of claim 3, wherein the animal subject is a mouse.

5. The method of claim 4, wherein the C-reactive protein is administered in a dose of about 200 µg.

6. The method of claim 1, wherein the administering is effected via a transcutaneous medicator.

7. The method of claim 1, wherein the administering is effected via subcutaneous injection.

8. The method of claim 1, wherein the administering is effected intravenously.

9. A method of treating kidney disease associated with systemic lupus erythematosus in a patient in need of treatment, comprising administering an effective amount of a therapeutic material chosen from a C-reactive protein, a metabolite of C-reactive protein, and a combination thereof to the patient for a time and under conditions effective to mitigate kidney disease associated with systemic lupus erythematosus.

10. A method of treating kidney disease associated with proteinuria in a patient in need of treatment, comprising administering an effective amount of a therapeutic material chosen from a C-reactive protein, a metabolite of C-reactive protein, and a combination thereof to the patient for a time and under conditions effective to mitigate kidney disease associated with proteinuria.

* * * * *

UNITED STATES PATENT AND TRADEMARK OFFICE
CERTIFICATE OF CORRECTION

PATENT NO.         : 7,226,995 B2
APPLICATION NO. : 10/947267
DATED                  : June 5, 2007
INVENTOR(S)        : Terry Du Clos and Carolyn Mold It is certified that error appears in the above-identified patent and that said Letters Patent is hereby corrected as shown below:

Column 1, lines 12-15: Change "This invention was made with government support under a VA merit review and grant R01-AI28358 awarded by the National Institutes of Health. The U.S. government may have certain rights in this invention." to --This invention was made with government support under a VA merit review and grant R01-AI028358 awarded by the National Institutes of Health. The U.S. government has certain rights in this invention.--

Claim 4, line 13: Change "The method of claim 3," to --The method of claim 1,--

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,226,995 B2
APPLICATION NO. : 10/947267
DATED : June 5, 2007
INVENTOR(S) : Terry Du Clos and Carolyn Mold It is certified that error appears in the above-identified patent and that said Letters Patent is hereby corrected as shown below:

Column 1, lines 12-15: Change "This invention was made with government support under a VA merit review and grant R01-AI28358 awarded by the National Institutes of Health. The U.S. government may have certain rights in this invention." to --This invention was made with government support under a VA merit review and grant R01-AI028358 awarded by the National Institutes of Health. The U.S. government has certain rights in this invention.--

Column 9, Claim 4, line 13: Change "The method of claim 3," to --The method of claim 1,--

This certificate supersedes the Certificate of Correction issued June 2, 2009.

Signed and Sealed this

Twenty-third Day of June, 2009

JOHN DOLL
*Acting Director of the United States Patent and Trademark Office*